United States Patent
Desjardins

[11] Patent Number: 5,236,162
[45] Date of Patent: Aug. 17, 1993

[54] PUMP SUPPORT SYSTEM

[76] Inventor: Wallace H. Desjardins, 352 Lake Blvd., Lindenwold, N.J. 08021

[21] Appl. No.: 393,836

[22] Filed: Aug. 14, 1989

Related U.S. Application Data

[63] Continuation of Ser. No. 153,970, Feb. 9, 1988, abandoned.

[51] Int. Cl.⁵ ............................................. A47C 21/00
[52] U.S. Cl. .................................................. 248/214
[58] Field of Search ...................... 248/214, 215, 309.2

[56] References Cited

U.S. PATENT DOCUMENTS

| | | | |
|---|---|---|---|
| 334,631 | 1/1886 | Adler | 248/214 |
| 624,809 | 5/1899 | Howe | 248/309.2 |
| 835,314 | 11/1906 | Oliver | 248/214 |
| 1,219,158 | 3/1917 | Rose | 5/507 X |
| 2,807,032 | 9/1957 | Tunney | 5/503 |
| 3,351,312 | 11/1967 | Ballas | 5/507 X |
| 3,648,830 | 3/1972 | Graf | 248/311.2 X |
| 3,809,349 | 5/1974 | Baedke | 248/215 X |
| 4,203,175 | 5/1980 | Heine | 5/503 |
| 4,418,496 | 12/1983 | Koistinen | 248/215 X |
| 4,504,992 | 3/1985 | Herron et al. | 5/507 X |
| 4,691,397 | 9/1987 | Netzer | 248/214 X |

Primary Examiner—Alvin C. Chin-Shue
Attorney, Agent, or Firm—Synnestvedt & Lechner

[57] ABSTRACT

A universal pump bracket incorporating a hanger is attached to each infusion pump in a hospital employing the system. A pump support element adapted to cooperatively receive the bracket hanger is mounted on each wheelchair, stretcher and on other fixed and portable pump receiving stations in the hospital. The transport of patients receiving intravenous medication is expedited with the system since an infusion pump may be safely demountably supported by the same device on which the patient is transported, eliminating the need for auxiliary roller stands and additional personnel.

2 Claims, 3 Drawing Sheets

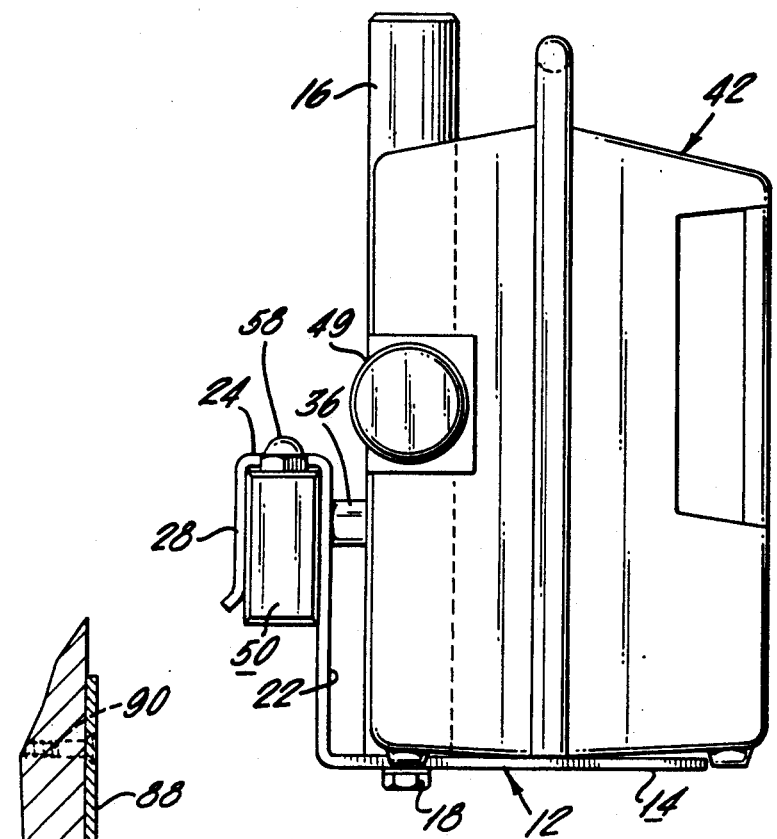
Fig. 3.
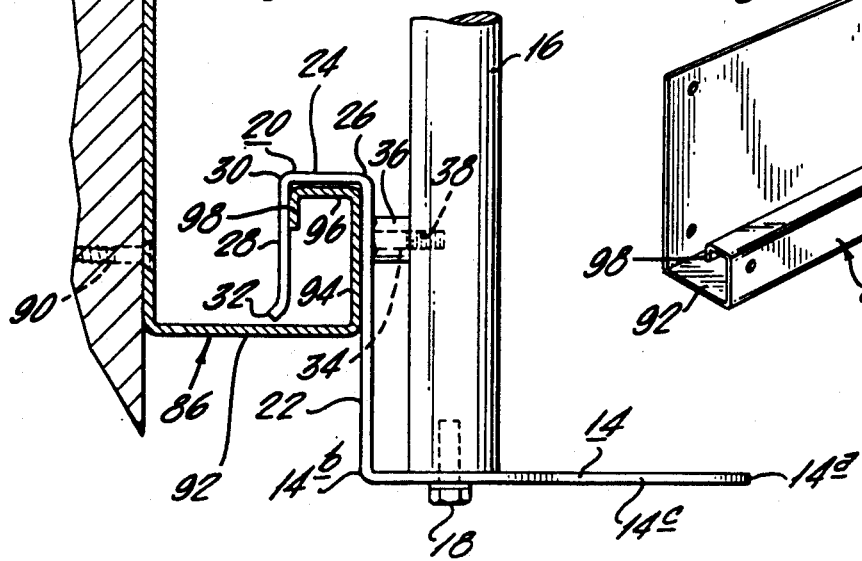
Fig. 4.
Fig. 5.

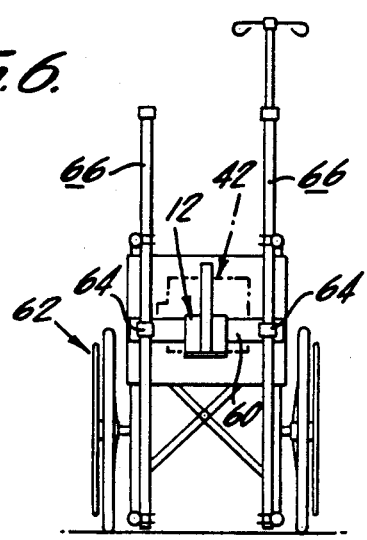
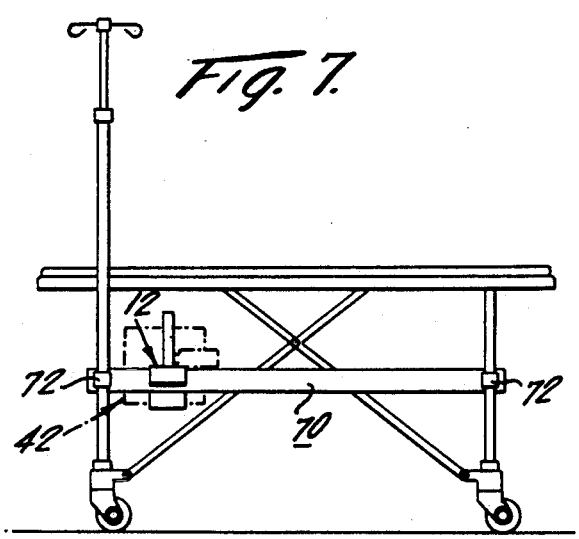
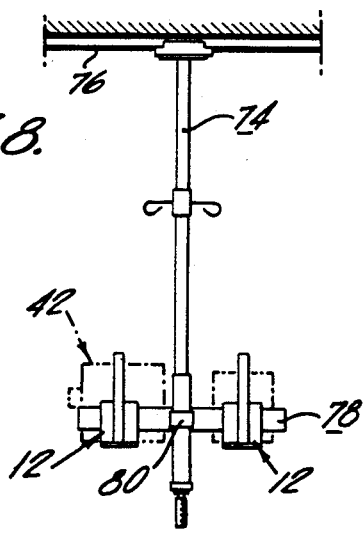
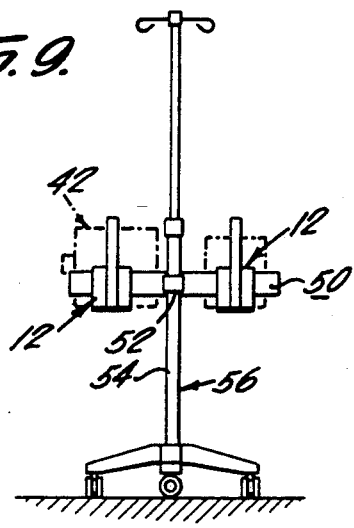
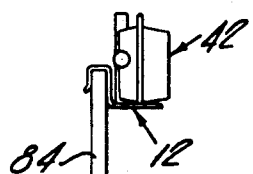

PUMP SUPPORT SYSTEM

This is a continuation of copending application Ser. No. 07/153,970, filed on Feb. 9, 1988, now abandoned.

BACKGROUND OF THE INVENTION

The present invention relates generally to hospital equipment and relates more particularly to a transport system for moving patients who are receiving intravenous medication from one or more infusion pumps.

The transport of hospital patients who are receiving intravenous medication has been an awkward and difficult task, usually requiring two or more people. Typically, the medication supply and the infusion pump controlling the intravenous flow are mounted on a separate stand which must be rolled closely adjacent the wheelchair or stretcher on which the patient is carried. The conventional practice is not only hazardous to the patient and the equipment, but in addition is an economic drain because of the number of skilled personnel required.

The patient suffers for a number of reasons with the conventional system. Transport is frequently delayed until a nurse is available to assist the transport aide. In many instances, such a transport from recovery rooms, the patient is experiencing nausea and/or other discomforts and any delay in transport causes unnecessary suffering and anxiety.

A more serious concern is the possibility that an infusion pump may be dropped or separated from the patient so as to cause a discontinuity in the flow of the intravenous solution. The opportunities for such a possibility becoming realized are frequent, considering the turns, ramps, doorways, elevators and congested corridors which usually must be negotiated in the course of a patient transport which might be a city block or more in length. Hospital corridors are often lined with carts and other equipment, and patients being transported often have difficulty passing other patients also undergoing transport. The resultant delays cause added anxiety for the patient, and may even pose fire hazard by completely blocking the corridor to passage by others.

The possibility of damage to equipment with the conventional patient transport practice is a real concern. If the infusion pump is moved on a pump stand, there is a danger of the stand toppling due to its short wheel base and top heavy condition, particularly when negotiating confined areas where engagement with obstructions is likely to trip the legs of the stand. Should the pump be transported by simply resting it on the stretcher or wheelchair, an even greater likelihood exists of the pump falling as the patient is moved around corners, moved along ramps or across uneven elevator threshholds or subjected to abrupt stopping or starting movements.

Although ideally a transport aide alone should be able to transport a patient from one point in a hospital to another, if accessories such as infusion pumps or oxygen systems are involved, one or more additional people, usually nurses, are typically involved in the transport. The use of nurses for such duty is an inefficient use of skilled staff time. With the current shortage of nurses and considering their relatively high hourly cost to the hospital, it does not make economic sense to employ nurses for routine patient transport.

With the present system, the infusion pump is safely secured by means of a bracket to a support element on the patient's wheelchair or stretcher during transport, eliminating the need for separate roller stands. Extra personnel are not needed, even if several in fusion pumps are involved, and the majority of patient transports can be handled by a single transport aide. Pump support elements compatible with the bracket at fixed locations or on portable devices permit the rapid transfer of the patient and pump to or from the wheelchair or stretcher.

SUMMARY OF THE INVENTION

The present invention comprises a universal bracket which is attached to each infusion pump in the hospital. Since most pumps are designed for attachment to the vertical pole of a pump stand, the bracket of the invention includes a short length of vertical pole comparable to that of a conventional stand, to which pole the pump is attached by means of its mounting mechanism, usually a clamping screw. The bracket includes a hanger portion having a substantially inverted U-shape which extends from the rear of the bracket and which is adapted to slip over a substantially horizontal pump support element. In a preferred embodiment of the invention, the pump support element comprises a horizontal bar of rectangular section which can be permanently mounted on each wheelchair, stretcher and pump stand in the hospital. Support elements may also be attached to the walls at certain stations in the hospital where patients are frequently brought for testing, such as adjacent to x-ray equipment and the like.

For transport of a patient receiving intravenous solution from a pump provided with the present bracket, the pump bracket hanger is simply placed over the pump support element on the patient's wheelchair or stretcher. The transport may be effected by only one person, usually a transportation aide, and skilled nursing help need not be wasted on transport services. Upon arrival at the patient's destination, the pump is transferred from the wheelchair or stretcher to another fixed or portable pump support element, such as a pump stand. The weight of the pump is sufficient to hold the bracket hanger securely on the pump support element without danger of accidental dislodgement.

It is accordingly a first object of the present invention to provide a patient support system which permits a patient dependent on intravenous medication to be transported in most cases by one unskilled person.

A further object of the invention is to provide a patient support system which permits the rapid transfer of an infusion pump between pump support elements mounted on wheelchairs, stretchers, roller stands, ceiling mounted supports or other fixed or portable supporting members.

Another object of the invention is to provide a system as described characterized by a universal infusion pump bracket which is attached to each pump in the system by means of the pump's own attachment mechanism.

Still another object of the invention is to provide a system as described which provides a high degree of security for the pump during patient transfer.

A further object of the invention is to provide a system as described which is compatible with conventional hospital equipment including pumps, pump support stands, and patient transport equipment.

A still further object of the invention is to provide a system as described of a relatively simple design which can be inexpensively manufactured and installed.

Additional objects and advantages of the invention will be more readily apparent from the following detailed description of an embodiment thereof.

BRIEF DESCRIPTION OF THE DRAWINGS

FIG. 3 is a side elevational view of the pump, bracket and pump element shown in FIG. 2;

FIG. 4 is a view partly in section showing an embodiment of a pump support element which is attachable to a wall or other vertical support surface and includes a universal bracket disposed thereon but without a pump;

FIG. 5 is a isometric view in reduced scale showing the support element of FIG. 4;

FIG. 6 is a rear elevational view of a wheelchair showing the which a pump equipped with a universal pump bracket in accordance with the invention can be mounted by means of a pump support element extending between IV poles mounted on the rear of the wheelchair;

FIG. 7 is a side elevational view of a stretcher showing the manner in which a pump support element extending between the stretcher legs can accommodate the universal pump bracket;

FIG. 8 is a side elevational view of a ceiling mounted IV pole equipped with a pump support element adapted to support a pair of infusion pumps equipped with the universal bracket of the invention;

FIG. 9 is a side elevational view of an IV bottle roller stand equipped with a pump support element adapted to support two infusion pumps equipped with the present universal bracket; and FIG. 10 shows a hospital bed with a pump equipped with the universal bracket mounted on the bed headboard.

DESCRIPTION OF THE PREFERRED EMBODIMENT

Figure 1:
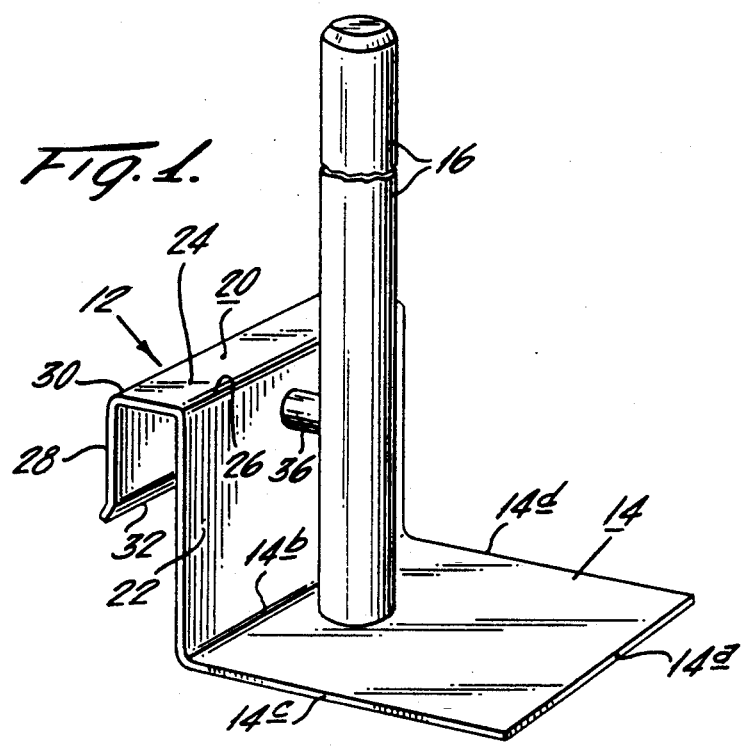
FIG. 1 is an isometric view of a universal infusion pump bracket in accordance with the present invention.

The present invention comprises a universal bracket 12 as shown in FIG. 1 which is adapted for attachment to an infusion pump by means of the pump's built in attachment mechanism. This mechanism typically involves a clamping screw for attaching the pump to a vertical pole such as the upstanding member of a roller stand. The bracket 12 comprises a horizontally disposed base plate 14 which in the illustrated embodiment is of a generally rectangular configuration. The plate 14, which is preferably made of sheet metal such as aluminum, includes a front edge 14a and a substantially parallel rear edge 14b, and side edges 14c and 14d.

Extending substantially perpendicularly from the upper surface of the plate 14 is a cylindrical pump mounting post 16 which is preferably of a lightweight metal such as aluminum. The post 16 is mounted on the plate 14 adjacent but spaced from the rear edge 14b thereof and centered between the side edges 14c and 14d. A screw 18 (FIG. 4) extends through an aperture in the plate into a threaded bore in the lower end of the post 16 to secure the post in position on the plate. The post 16 is of a sufficient height to permit attachment thereto of conventional infusion pumps when the bottom of the pump is seated on the plate 14 as will be presently described.

The bracket 12 includes a hanger 20 at the rear thereof permitting the demountable application of the bracket and attached pump to a pump support element by simply lowering the bracket onto the support element. The hanger 20 has an inverted U-shaped configuration and in the illustrated embodiment of the bracket comprises an extension of the plate 14 from its rear edge 14b, which extension comprises a vertical portion 22 formed by bending the extension of the plate upwardly at right angles along the edge 14b. The hanger 20 further includes a rearwardly directed horizontal portion 24 formed by bending the extending plate at right angles along an edge 26, and a further downwardly directed portion 28 formed by bending the extending plate at right angles along an edge 30. The hanger portion 28 terminates in a substantially horizontal edge 32 which is flared rearwardly for a purpose which will be evident from the discussion below. The vertical extent of the hanger portion 28 is approximately half that of the hanger portion 22. To facilitate manufacture, the width of the hanger is the same as the plate 14, and the plate and hanger are preferably formed from a single sheet of metal which is bent into the configuration illustrated.

Figure 2:
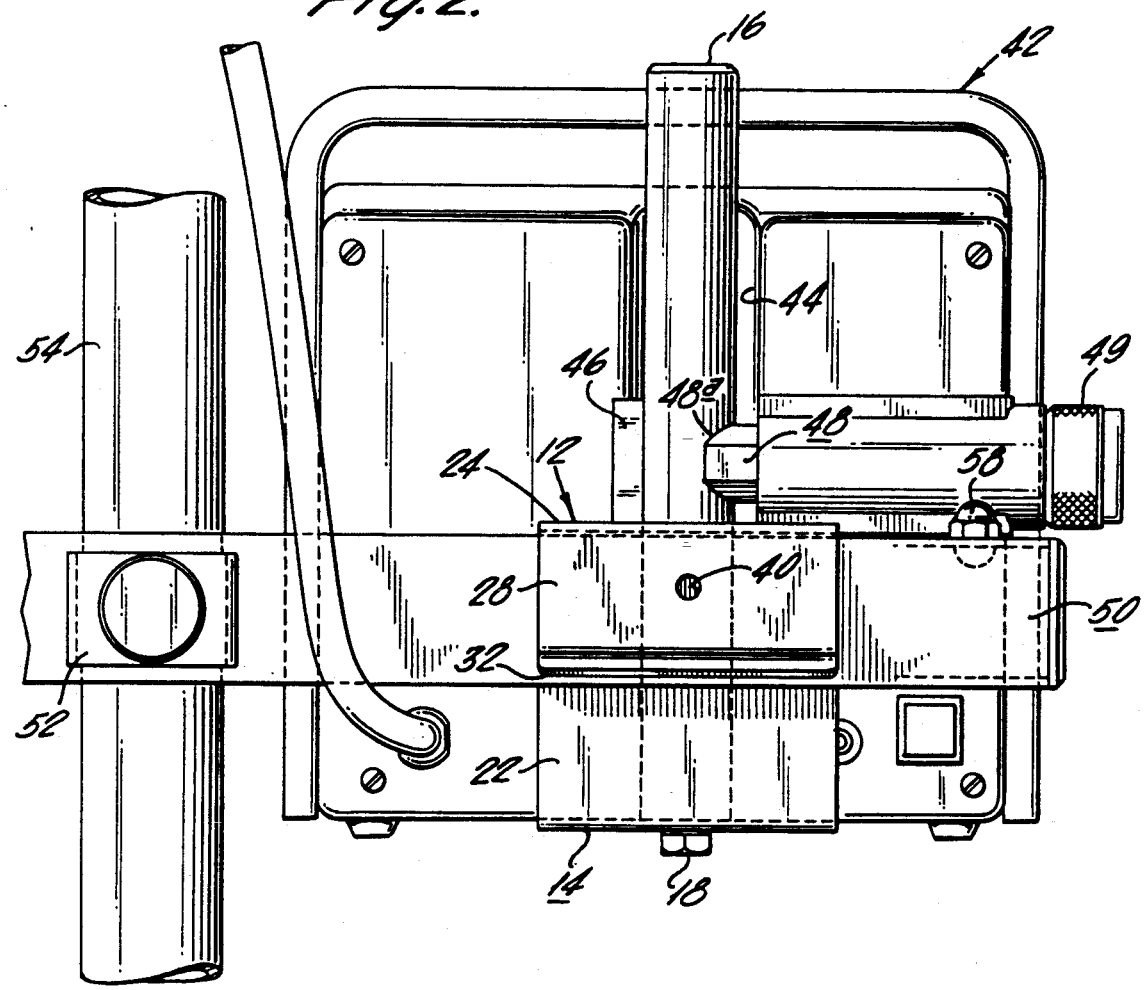
FIG. 2 is a rear view of an infusion pump equipped with the bracket of FIG. 1 and showing the pump supported by the bracket on a pump support element fixed to the vertical member of an infusion pump stand.

To provide additional rigidity to the pump mounting post 16, a screw 34 (FIG. 4) extends through the hanger portion 22 near the upper edge thereof, through a bore in a spacer 36, and into a threaded bore 38 in the post. As shown in FIG. 2, a hole 40 is provided in the hanger portion 28 aligned with the screw hole in the panel portion 22 to permit installation of the screw 34.

In accordance with the present system, a universal bracket of the type described will be attached to every infusion pump in a hospital employing the system. This attachment is accomplished by means of the pump's built-in pole clamping system which typically includes a clamping screw adapted to engage a cylindrical post. In FIGS. 2 and 3, a conventional type of infusion pump 42 is shown mounted on a bracket 12 with the bottom of the pump seated on the bracket plate 14. The pump 42 includes a vertical slot 44 at the rear thereof into which the bracket post 16 is disposed. A clamping shoe 46 on one side of the slot 44 provides a seating surface configured to cooperatively engage the post 16, and a clamping finger 48 disposed opposite the shoe 46 is brought into clamping contact with the post 16 by means of a screw mechanism controlled by a knurled clamping knob 49. The finger 48 includes a clamping surface 48a which is also configured to cooperatively engage the surface of the post 16. By tightening the knob 49, the pump is securely attached to the bracket and remains so attached throughout the employment of the pump in the present system. The bracket may, of course, be quickly removed from the pump should this be required, for example, to service the pump.

Pump support elements are provided at strategic locations in the hospital and on patient transport equipment such as wheelchairs and stretchers to support the bracket-equipped pump. The pump support elements may take different forms within the system, but have in common the ability to receive the hanger portion of the bracket in close fitting relation. Although the pump support element may take the form of a horizontal bar attached to various pieces of equipment, it may also comprise the headboard or footboard of a patient's bed, the leg bracing structure of a stretcher, or a wall mount bracket provided for such purpose. Several types of pump support elements will accordingly be described.

The pump support element of FIGS. 2 and 3 comprises a horizontal arm 50 comprising a rectangular metal tube, preferably aluminum, which fits snugly within the confines of the hanger 20 of the pump bracket. The arm 50 may be attached by means of a clamp 52 to the vertical post 54 of a roller stand of the conventional type 56 shown in FIG. 9 which typically include an adjustable IV bottle holder at its upper end. As shown in FIG. 9, the arm 50 may extend on each side of the pole, permitting the mounting of two or more pumps equipped with the present bracket.

The attachment of the pump to the support element simply involves the sliding of the hanger portion downwardly over the support element. The considerable weight of the pump, typically about 14 pounds, prevents its vertical dislodgement and friction prevents the sliding moving of the hanger horizontally along the support element. A plastic coating such as polypropylene, nylon or the like is preferably sprayed on the support element to increase the friction between pump bracket and support element. If additional security is desired, a screw such as the set screw the acorn head nut 58 shown in FIGS. 2 and 3 can be provided on the ends of the pump support element to prevent a pump from sliding off the end of the element or, perhaps more importantly, being placed too close to the end. In practice, the heavy weight of the pump and the close fit between the bracket hanger and the support element are sufficient to prevent any sliding movement of the pump.

A support element such as the bar described in FIGS. 2, 3 and 9 is also mounted on other equipment in a hospital employing the present system and particularly other mobile equipment such as wheelchairs and stretchers. In FIG. 6, a pump support element in the form of a horizontal bar 60 is attached to the rear of a wheelchair 62 by clamps 64 attached to spaced IV poles 66. A pump equipped with the bracket 12 may thus accompany a patient in the wheelchair receiving an intravenous medication from the pump by simply placing the pump bracket hanger over the bar 60. Since infusion pumps have auxiliary battery power, the usual AC power source is disconnected during patient transport. With the pump secured directly to the wheelchair, the need for a separate roller stand and an additional helper to move the stand is eliminated during wheelchair transport with the present system. The patient undergoing intravenous medication may thus be safely transported in a wheelchair by a single attendant.

In FIG. 7, a pump support element 70 in the form of an elongated horizontal bar is shown attached to the legs of a stretcher by clamps 72 and permits the carriage of one or more infusion pumps beneath the patient support surface and internally of the stretcher outer edges. The pump is accordingly safely positioned and securely held during patient transport and the need for an auxiliary support pole and additional personnel is eliminated.

In FIG. 8, a ceiling mounted IV pole 74 slideable along ceiling rails 76 includes a pump support element 78 in the form of a horizontal bar, attached to the pole by clamp 80. The support element 78 as illustrated may support two or more pumps and functions in a manner similar to that of FIGS. 2, 3 and 9.

In FIG. 10, a hospital bed 82 is shown with a pump 42 and bracket 12 disposed on the headboard 84 of the bed which serves effectively as the pump support element for a patient in the bed, and is particularly useful when bed transport is required due to patient acuity. The thickness of the headboard should substantially fill the space between the portions 22 and 28 of the bracket hanger.

In FIGS. 4 and 5, a further form of pump support element is illustrated in the form of a wall mounted pump support 86. In this embodiment, the element is formed of a single sheet of sheet metal including a back panel 88 attached to a wall by means of screws 90. The element 86 further includes a horizontal portion 92, an upright portion 94 extending vertically upwardly from the forward edge of the portion 92, a horizontal portion 96 extending rearwardly from the upper edge of the portion 94, and a downwardly directed portion 98 extending from the rear edge of the portion 96. As shown in FIG. 4, this forms an upstanding bar-like structure over which the hanger of the clamp may be securely deposited. Placement and removal of a pump equipped with the bracket is the same as previous embodiments, the bracket hanger simply being slid downwardly over the upstanding structure to provide a positive support for the pump. The wall mount may be used in a variety of locations such as in a waiting area where a patient undergoing intravenous medication may be awaiting testing. Such a bracket may also be used adjacent a patient's bed to hold one or more pumps.

The rearward angling of the edge 32 of the bracket hanger facilitates the placement of the hanger over the support element, particularly if the clearance between the bracket and support element is small.

A significant advantage of the invention from the standpoint of economy is the permissible fabrication of the bracket and support element parts from stock materials. For example, the support elements may be cut from one inch by two inch aluminum tube stock while the base plate and hanger may be formed from one eighth inch sheet aluminum. The post 16 is similarly cut from standard size aluminum bar stock. Since a minimal number of machining and assembly operations are required, the cost of the system is relatively low and can be recouped by the saving in skilled staff time in a short period.

The bracket base plate 14 is provided more as a safety element than as a necessity since the pump attachment to the post 16 should in itself be sufficient to hold the pump to the bracket. However, for ease in initially locating the pump on the post and to provide a safety feature in case the pump should slip on the post, the plate 14 is provided beneath the bottom of the pump. In a modified embodiment, the plate 14 could be eliminated and the post be attached solely to the hanger such as by a second screw spaced below the screw 34. In such embodiment, the lower end of the post could be provided with an enlargement of some type to prevent the pump from falling to the floor in the event of slippage of the attachment screw.

From the foregoing it can be appreciated that the present system provides an effective and economical solution to the problems of conventional patient transport. Not only can patients be safely transported by a single transport aide, but the transport itself is faster since there is no need to coordinate patient movement with the usual auxiliary pump stands. The pump itself is safely secured during transport in a protected area and the possibility of pump damage is minimized. The system due to the ease of use of the universal bracket and pump support elements, also greatly facilitates the transfer of the pump to and from a pump stand or wall bracket at the beginning and end of transport, thereby quickly freeing the transport aide for other duties. Instead of screwing or unscrewing the pump mount each time the pump is moved, with the present system the bracket hanger need only be placed over the support element and the pump released.

Manifestly, changes in details of construction can be effected by those skilled in the art without departing from the invention.

I claim:

1. A portable infusion pump assembly suitable for carrying from place to place as a unit, by one person, comprising:

a portable infusion pump for administering fluid to patients;

a portable mounting bracket secured to and carried by said pump as said pump is moved from one location to another;

said mounting bracket comprising a hanger portion forming a downwardly-facing channel permitting temporary hanging of said pump assembly on any selected one of a plurality of horizontal supports, and permitting subsequent unitary liftoff of said pump assembly from the selected support for subsequent unitary transport to, and hanging upon, another of said supports;

wherein said bracket comprises a horizontal base portion and a post fixedly secured to and extending upwardly from said base portion for unitary transport with said bracket, said pump being secured to said post with its bottom adjacent said base portion of said bracket, said channel portion constituting an integral extension of said base plate, and said bracket having a width not substantially greater than that of said pump.

2. A hospital system, comprising:

a plurality of wheeled patient-transport vehicles;

a plurality of unitary portable infusion pump assemblies;

a horizontal support means on each of said vehicles, for supporting any one of said pump assemblies;

each of said assemblies comprising a unitary combination of one of said infusion pumps and a bracket secured thereto and adapted to fit demountably onto any of said support means of any of said vehicles, each of said assemblies being thus mountable on or demountable from any of said support means without disassembly of the pump from the bracket;

wherein each said bracket comprises a base plate and a post affixed thereto and extending upwardly therefrom, the corresponding pump being mounted to the portion of said post adjacent to said base plaste, said bracket also comprising a hanger portion integral with said base plate and having the general shape of an inverted U, said hanger portion having a configuration such as to fit over and rest upon any of said horizontal support means, said bracket having a width not substantially greater than the width of said pump means.

* * * * *